(12) United States Patent
Mun et al.

(10) Patent No.: US 11,286,964 B2
(45) Date of Patent: Mar. 29, 2022

(54) SOFT ACTUATOR AND ARTIFICIAL MUSCLE INCLUDING THE SAME

(71) Applicant: Electronics and Telecommunications Research Institute, Daejeon (KR)

(72) Inventors: Seongcheol Mun, Sejong-si (KR); Sungryul Yun, Daejeon (KR); Jeong Muk Lim, Daejeon (KR); Inwook Hwang, Sejong-si (KR)

(73) Assignee: ELECTRONICS AND TELECOMMUNICATIONS RESEARCH INSTITUTE, Daejeon (KR)

(*) Notice: Subject to any disclaimer, the term of this patent is extended or adjusted under 35 U.S.C. 154(b) by 0 days.

(21) Appl. No.: 17/116,665

(22) Filed: Dec. 9, 2020

(65) Prior Publication Data

US 2021/0180620 A1 Jun. 17, 2021

(30) Foreign Application Priority Data

Dec. 11, 2019 (KR) .................. 10-2019-0164698
Nov. 27, 2020 (KR) .................. 10-2020-0162090

(51) Int. Cl.
*F15B 15/10* (2006.01)
*A61F 2/08* (2006.01)

(52) U.S. Cl.
CPC .............. *F15B 15/103* (2013.01); *A61F 2/08* (2013.01)

(58) Field of Classification Search
CPC .................. F15B 15/103; A61F 2/08
See application file for complete search history.

(56) References Cited

U.S. PATENT DOCUMENTS

| 10,446,330 | B2 | 10/2019 | Kim et al. | |
| 10,892,690 | B2* | 1/2021 | Van Den Ende | H02N 2/025 |
| 2007/0257582 | A1* | 11/2007 | Yokoyama | H02N 1/002 |
| | | | | 310/300 |
| 2016/0206420 | A1 | 7/2016 | Yun et al. | |
| 2018/0138833 | A1 | 5/2018 | Van Den Ende et al. | |
| 2018/0263839 | A1 | 9/2018 | Lim et al. | |
| 2019/0348596 | A1* | 11/2019 | Pelssers | H01L 41/183 |
| 2020/0039200 | A1 | 2/2020 | Doernhoefer et al. | |

FOREIGN PATENT DOCUMENTS

| KR | 10-1172427 | 8/2012 |
| KR | 10-2014-0103092 | 8/2014 |
| KR | 10-1660116 | 9/2016 |
| KR | 10-2018-0015682 | 2/2018 |
| KR | 10-2019-0137134 | 12/2019 |

* cited by examiner

*Primary Examiner* — Michael Leslie
*Assistant Examiner* — Daniel S Collins
(74) *Attorney, Agent, or Firm* — Kile Park Reed & Houtteman PLLC

(57) ABSTRACT

Provided is a soft actuator. The soft actuator includes a first bistable polymer layer, a second bistable polymer layer on the first bistable polymer layer, a first flexible electrode layer on an upper surface of the second bistable polymer layer, a second flexible electrode layer between the first bistable polymer layer and the second bistable polymer layer, a first light absorption heating layer disposed on the first flexible electrode layer and configured to increase a temperature when light is absorbed, and a first voltage supply unit, wherein the first voltage supply unit is electrically connected to the first flexible electrode layer and the second flexible electrode layer.

13 Claims, 8 Drawing Sheets

SOFT ACTUATOR AND ARTIFICIAL MUSCLE INCLUDING THE SAME

CROSS-REFERENCE TO RELATED APPLICATIONS

This U.S. non-provisional patent application claims priority under 35 U.S.C. § 119 of Korean Patent Application Nos. 10-2019-0164698, filed on Dec. 11, 2019, and 10-2020-0162090, filed on Nov. 27, 2020, the entire contents of which are hereby incorporated by reference.

BACKGROUND

The present disclosure herein relates to a soft actuator and an artificial muscle including the same, and more particularly, to a soft actuator capable of precise control and an artificial muscle including the same.

Artificial muscle is artificially created by imitating actual muscle and refers to a substance or device that shows movement in stimuli such as voltage, current, temperature, and pressure. Artificial muscle technology is being developed in a variety of materials and structures such as shape memory alloy (SMA), electroactive polymer (EAP), and yarn-structured polymer nanomaterial composites, starting with the McKibben air muscle, which contracts and relaxes while supplying compressed air inside the tube. Electroactive polymers are materials that move when voltage is applied, and have various advantages such as fast response speed, large deformation, low power consumption, and excellent processability, and the principles and characteristics most similar to those of the human body. Therefore, despite the limitation of low output, it is most often studied as an artificial muscle technology. Electroactive polymers may be divided into ionic EAP and field activated EAP according to their operation method. When a voltage is applied to the ionic polymer, flexing deformation (bending) occurs due to the volume difference generated as the ions move in the direction of the electrode having opposite charges. Field activated EAP undergoes an electron polarization phenomenon by an applied electric field and is deformed by electrostatic force caused by electric charges induced in both electrodes. Among them, dielectric elastomers are artificial muscle materials that are attracting the most attention for their very large amount of deformation and stress, fast response speed, durability, and excellent reproducibility compared to EAP.

SUMMARY

The present disclosure provides a soft actuator capable of precise control and an artificial muscle including the same.

The present disclosure also provides a soft actuator having a small volume and slimming, and an artificial muscle including the same.

The present also disclosure also provides a soft actuator capable of bending with a plurality of curvatures and an artificial muscle including the same.

The problem to be solved by the inventive concept is not limited to the problems mentioned above, and other problems that are not mentioned will be clearly understood by those skilled in the art from the following description.

An embodiment of the inventive concept provides a soft actuator including: a first bistable polymer layer; a second bistable polymer layer on the first bistable polymer layer; a first flexible electrode layer on an upper surface of the second bistable polymer layer; a second flexible electrode layer between the first bistable polymer layer and the second bistable polymer layer; a first light absorption heating layer disposed on the first flexible electrode layer and configured to increase a temperature when light is absorbed; and a first voltage supply unit, wherein the first voltage supply unit is electrically connected to the first flexible electrode layer and the second flexible electrode layer.

In an embodiment, the first light absorption heating layer may include a PEDOT-based material.

In an embodiment, the soft actuator may further include a third flexible electrode layer on a lower surface of the first bistable polymer layer.

In an embodiment, the soft actuator may further include a second light absorption heating layer coupled under the third flexible electrode layer.

In an embodiment, the soft actuator may further include a second voltage supply unit, wherein the second voltage supply unit may be electrically connected to the second flexible electrode layer and the third flexible electrode layer.

In an embodiment, the soft actuator may further include a support structure part coupled to an upper surface of the first light absorption heating layer and a side surface of the second bistable polymer layer.

In an embodiment of the inventive concept, an artificial muscle includes: a soft actuator; a light source; and a control unit, wherein the soft actuator includes: a first bistable polymer layer; a second bistable polymer layer on the first bistable polymer layer; a first flexible electrode layer on an upper surface of the second bistable polymer layer; a second flexible electrode layer between the first bistable polymer layer and the second bistable polymer layer; a first light absorption heating layer disposed on the first flexible electrode layer and configured to increase a temperature when light is absorbed; a first voltage supply unit; and a support structure part coupled to an upper surface of the first light absorption heating layer and a side surface of the second bistable polymer layer, wherein the first voltage supply unit is electrically connected to the first flexible electrode layer and the second flexible electrode layer, wherein the control unit controls the light source and the first voltage supply unit.

In an embodiment, the artificial muscle may further include: a third flexible electrode layer on a lower surface of the first bistable polymer layer; and a second light absorption heating layer coupled under the third flexible electrode layer.

In an embodiment, the artificial muscle may further include a second voltage supply unit, wherein the second voltage supply unit may be electrically connected to the second flexible electrode layer and the third flexible electrode layer.

In an embodiment, each of the first light absorption heating layer and the second light absorption heating layer may include a PEDOT-based material.

In an embodiment, the light source may include a first light source that irradiates light to the first light absorption heating layer and a second light source that irradiates light to the second light absorption heating layer.

In an embodiment of the inventive concept, an artificial muscle includes: a soft actuator; and a light source configured to irradiate light to the soft actuator, wherein the soft actuator includes: a bistable polymer layer; a first flexible electrode layer on an upper surface of the bistable polymer layer; a second flexible electrode layer on a lower surface of the bistable polymer layer; a light absorption heating layer disposed on the first flexible electrode layer and configured to increase a temperature when light is absorbed; and a voltage supply unit, wherein the voltage supply unit is electrically connected to the first flexible electrode layer and the second flexible electrode layer, wherein the light absorption heating layer is patterned, so that a part of the first flexible electrode layer is exposed between the patterned light absorption heating layer.

In an embodiment, the light absorption heating layer may include a PEDOT-based material.

In an embodiment, the artificial muscle may further include a support structure part coupled to an upper surface of the light absorption heating layer or a side surface of the second bistable polymer layer.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

Figure 1:
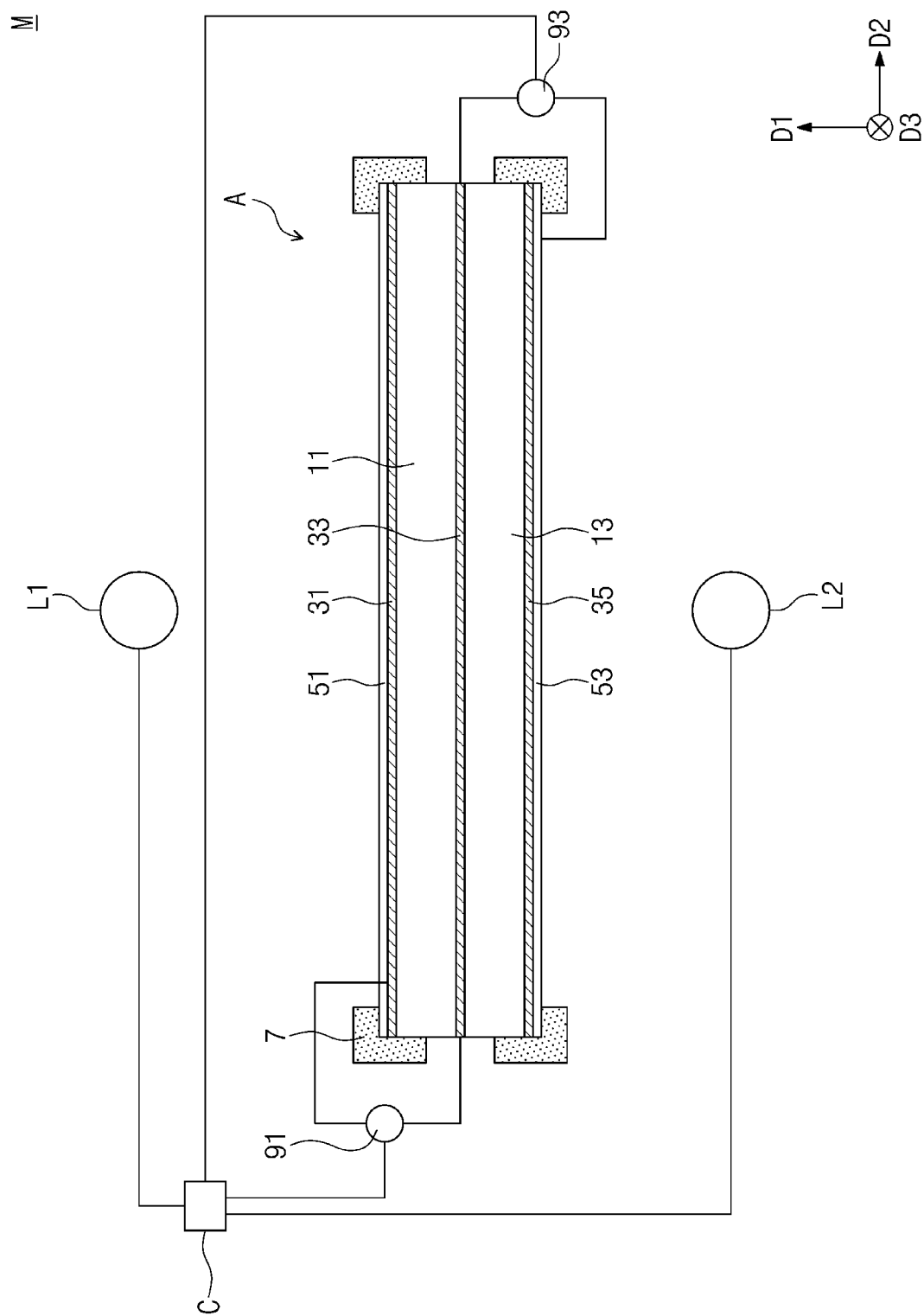
FIG. 1 is a cross-sectional view showing a soft actuator and an artificial muscle including the same according to an exemplary embodiment of the inventive concept.

In order to fully understand the configuration and effect of the technical idea of the inventive concept, preferred embodiments of the technical idea of the inventive concept will be described with reference to the accompanying drawings. However, the technical idea of the inventive concept is not limited to the embodiments disclosed below, but may be implemented in various forms and various changes may be added. However, it is provided to completely disclose the technical idea of the inventive concept through the description of the present embodiments, and to fully inform a person of ordinary skill in the art to which the inventive concept belongs.

Like reference numerals refer to like elements throughout the specification. Embodiments described in the present specification will be described with reference to a block diagram, a perspective view, and/or a cross-sectional view, which are ideal exemplary diagrams of the technical idea of the inventive concept. In the drawings, the thicknesses of regions are exaggerated for effective description of technical content. Accordingly, the regions illustrated in the drawings have schematic properties, and the shapes of the regions illustrated in the drawings are intended to illustrate a specific shape of the device region and are not intended to limit the scope of the invention. In various embodiments of the present specification, various terms are used to describe various components, but these components should not be limited by such terms. These terms are only used to distinguish one component from another component. The embodiments described and illustrated herein also include complementary embodiments thereof.

The terms used in this specification are for describing exemplary embodiments and are not intended to limit the inventive concept. In this specification, the singular form also includes the plural form unless specifically stated in the phrase. As used in the specification, "comprises" and/or "comprising" do not exclude the presence or addition of one or more other elements.

Hereinafter, the inventive concept will be described in detail by describing preferred embodiments of the technical idea of the inventive concept with reference to the accompanying drawings.

FIG. 1 is a cross-sectional view showing a soft actuator and an artificial muscle including the same according to an exemplary embodiment of the inventive concept.

Hereinafter, D1 in FIG. 1 may be referred to as a first direction, D2 crossing the first direction D1 may be referred to as a second direction, and D3 may be referred to as a third direction.

Referring to FIG. 1, artificial muscle M may be provided. The artificial muscle M may provide power to move the human body instead of some of the muscles of the human body. In embodiments, the artificial muscle M may include a soft actuator A, a light source, and a control unit C.

The soft actuator A may have a function of moving the artificial muscle M. However, the inventive concept is not limited thereto, and the soft actuator A may be used for other purposes. In embodiments, the soft actuator A may include a first bistable polymer layer 13, a second bistable polymer layer 11, a first flexible electrode layer 31, a second flexible electrode layer 33, a third flexible electrode layer 35, a first light absorption heating layer 51, a second light absorption heating layer 53, a first voltage supply unit 91, a second voltage supply unit 93, and a support structure part 7.

The first bistable polymer layer 13 may extend in the second direction D2. The first bistable polymer layer 13 may include a material whose rigidity changes according to temperature. For example, the first bistable polymer layer 13 may include a bistable dielectric polymer material whose rigidity decreases when the temperature increases. In embodiments, the bistable dielectric polymer material may refer to a polymer material that may exist in a stable state in two temperature ranges. Therefore, the first bistable polymer layer 13 is present while maintaining a certain rigidity at a certain temperature, and the rigidity may change when the temperature rises and reaches another temperature range. That is, when the temperature of the first bistable polymer layer 13 increases, the rigidity of the first bistable polymer layer 13 may change.

The second bistable polymer layer 11 may be positioned on the first bistable polymer layer 13. More specifically, the second bistable polymer layer 11 may be bonded on the first bistable polymer layer 13 using the second flexible electrode layer 33 as a medium. The second bistable polymer layer 11 may extend in the second direction D2. The second bistable polymer layer 11 may include a material whose rigidity changes according to temperature. For example, the second bistable polymer layer 11 may include a bistable dielectric polymer material whose rigidity decreases when the temperature increases.

The first flexible electrode layer 31 may be positioned on the second bistable polymer layer 11. The first flexible electrode layer 31 may extend in the second direction D2. The first flexible electrode layer 31 may include a flexible conductive material. Therefore, the first flexible electrode layer 31 may be bent. The first flexible electrode layer 31 may be electrically connected to the first voltage supply unit 91.

The second flexible electrode layer 33 may be positioned between the first bistable polymer layer 13 and the second bistable polymer layer 11. The second flexible electrode layer 33 may extend in the second direction D2. The second flexible electrode layer 33 may include a material that is substantially the same as or similar to that of the first flexible electrode layer 31. Accordingly, the second flexible electrode layer 33 may include a conductive material. The second flexible electrode layer 33 may be electrically connected to the first voltage supply unit 91 and/or the second voltage supply unit 93.

The third flexible electrode layer 35 may be located on the lower surface of the first bistable polymer layer 13. The third flexible electrode layer 35 may extend in the second direction D2. The third flexible electrode layer 35 may include a material that is substantially the same as or similar to that of the first flexible electrode layer 31. Therefore, the third flexible electrode layer 35 may include a conductive material. The third flexible electrode layer 35 may be electrically connected to the second voltage supply unit 93.

The first light absorption heating layer 51 may be located on the first flexible electrode layer 31. The first light absorption heating layer 51 may extend in the second direction D2. The first light absorption heating layer 51 may absorb light and increase the temperature. That is, when light is irradiated to the first light absorption heating layer 51, the temperature of the first light absorption heating layer 51 may increase. The first light absorption heating layer 51 may include a material having high absorption of light in the near-infrared wavelength band. For example, the first light absorption heating layer 51 may include a poly(3,4-ethylenedioxythiophene) (PEDOT)-based material. However, the inventive concept is not limited thereto.

The second light absorption heating layer 53 may be located under the third flexible electrode layer 35. The second light absorption heating layer 53 may extend in the second direction D2. The second light absorption heating layer 53 may absorb light and increase the temperature. That is, when light is irradiated to the second light absorption heating layer 53, the temperature of the second light absorption heating layer 53 may increase. The second light absorption heating layer 53 may include a material having high absorption of light in the near infrared wavelength band. For example, the second light absorption heating layer 53 may include a poly(3,4-ethylenedioxythiophene) (PEDOT)-based material. However, the inventive concept is not limited thereto.

The first voltage supply unit 91 may be electrically connected to the first flexible electrode layer 31 and the second flexible electrode layer 33. The first voltage supply unit 91 may supply voltage to the first flexible electrode layer 31 and the second flexible electrode layer 33. By the voltage provided by the first voltage supply unit 91, the second bistable polymer layer 11 may be bent. Details on this will be described later.

The second voltage supply unit 93 may be electrically connected to the third flexible electrode layer 35 and the second flexible electrode layer 33. The second voltage supply unit 93 may supply voltage to the third flexible electrode layer 35 and the second flexible electrode layer 33. By the voltage provided by the second voltage supply unit 93, the first bistable polymer layer 13 may be bent. Details on this will be described later.

The support structure part 7 may be coupled on the side surfaces of the first and second bistable polymer layers 13 and 11, the side surfaces of the first to third flexible electrode layers 31, 33, and 35, and/or the side surface and the upper surfaces of the first and second light absorption heating layers 51 and 53. The support structure part 7 may be coupled to an external configuration. The soft actuator A made of a flexible material may be connected to an external configuration by the support structure part 7.

The light source may irradiate light to the first light absorption heating layer 51 and/or the second light absorption heating layer 53. In embodiments, a plurality of light sources may be provided. For example, the light source may include a first light source L1 and a second light source L2. The first light source L1 may be spaced upward from the first light absorption heating layer 51. The first light source L1 may irradiate light toward the first light absorption heating layer 51. The second light source L2 may be spaced downward from the second light absorption heating layer 53. The second light source L2 may irradiate light toward the second light absorption heating layer 53. Although it has been described above that two light sources are provided, the inventive concept is not limited thereto. That is, one light source may be provided, or three or more light sources may be provided. In embodiments, a plurality of light sources may be spaced apart in a horizontal direction. That is, the light sources may be disposed to be spaced apart from each other in the second direction D2 and/or the third direction D3. Light sources spaced apart in the horizontal direction may irradiate light to different portions of the light absorption heating layer. Accordingly, at different points in the horizontal direction within one light absorption heating layer, the light absorption heating layer may be deformed into different shapes. That is, one light absorption heating layer may be bent with various curvatures. Details on this will be described later.

The control unit C may control the light sources L1 and L2 and the first and second voltage supply units 91 and 93. Under the control of the control unit C, the light sources L1 and L2 irradiate light to the first and second light absorption heating layers 51 and 53, or the first and second voltage supply units 91 and 93 may supply voltage to the first, second and third flexible electrode layers 31, 33 and 35.

Figure 2:
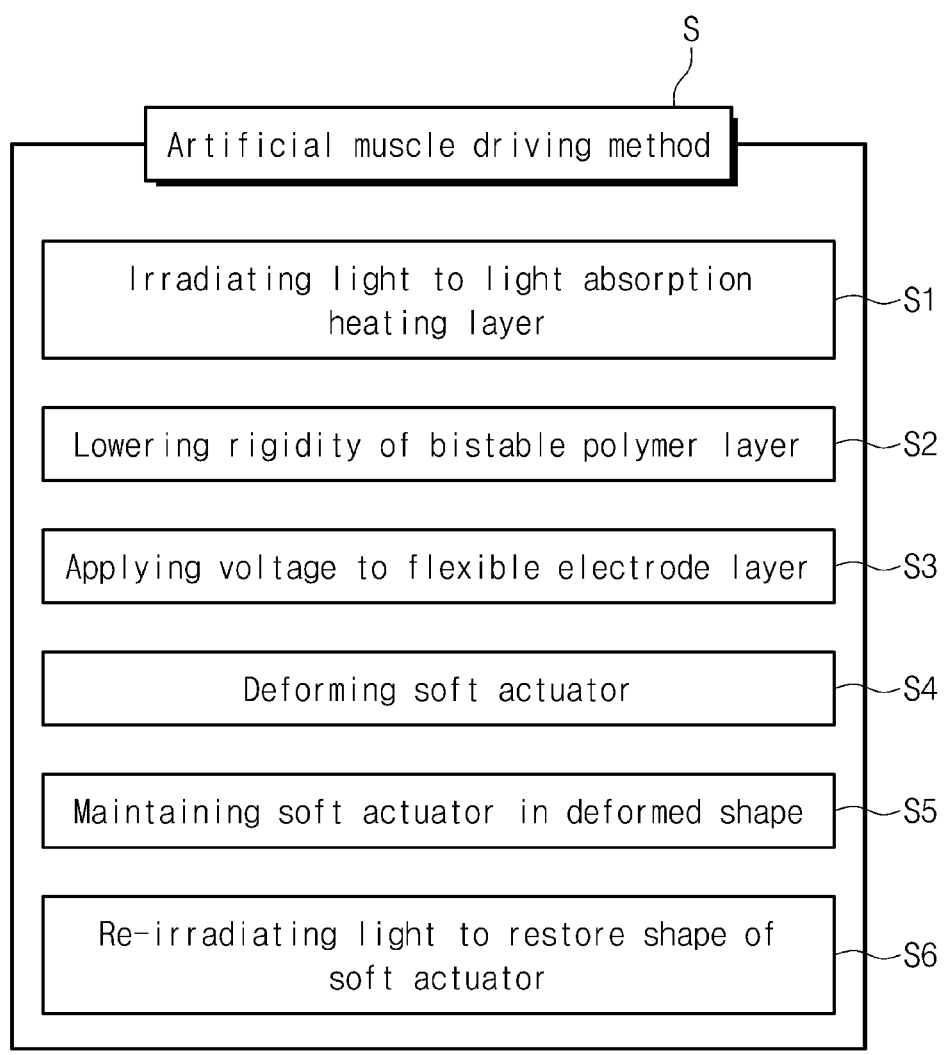
FIG. 2 is a flowchart showing a method of using a soft actuator and an artificial muscle including the same according to an exemplary embodiment of the inventive concept.

FIG. 2 is a flowchart showing a method of using a soft actuator and an artificial muscle including the same according to an exemplary embodiment of the inventive concept.

Referring to FIG. 2, the artificial muscle driving method S may be provided. The artificial muscle driving method S may include irradiating light to the light absorption heating layer S1, lowering the rigidity of the bistable polymer layer S2, applying voltage to the flexible electrode layer S3, deforming the soft actuator S4, maintaining the soft actuator in the deformed shape S5, and re-irradiating light to restore the shape of the soft actuator S6. Hereinafter, each operation of the artificial muscle driving method S will be described in detail with reference to FIGS. 3 and 4.

Figure 3:
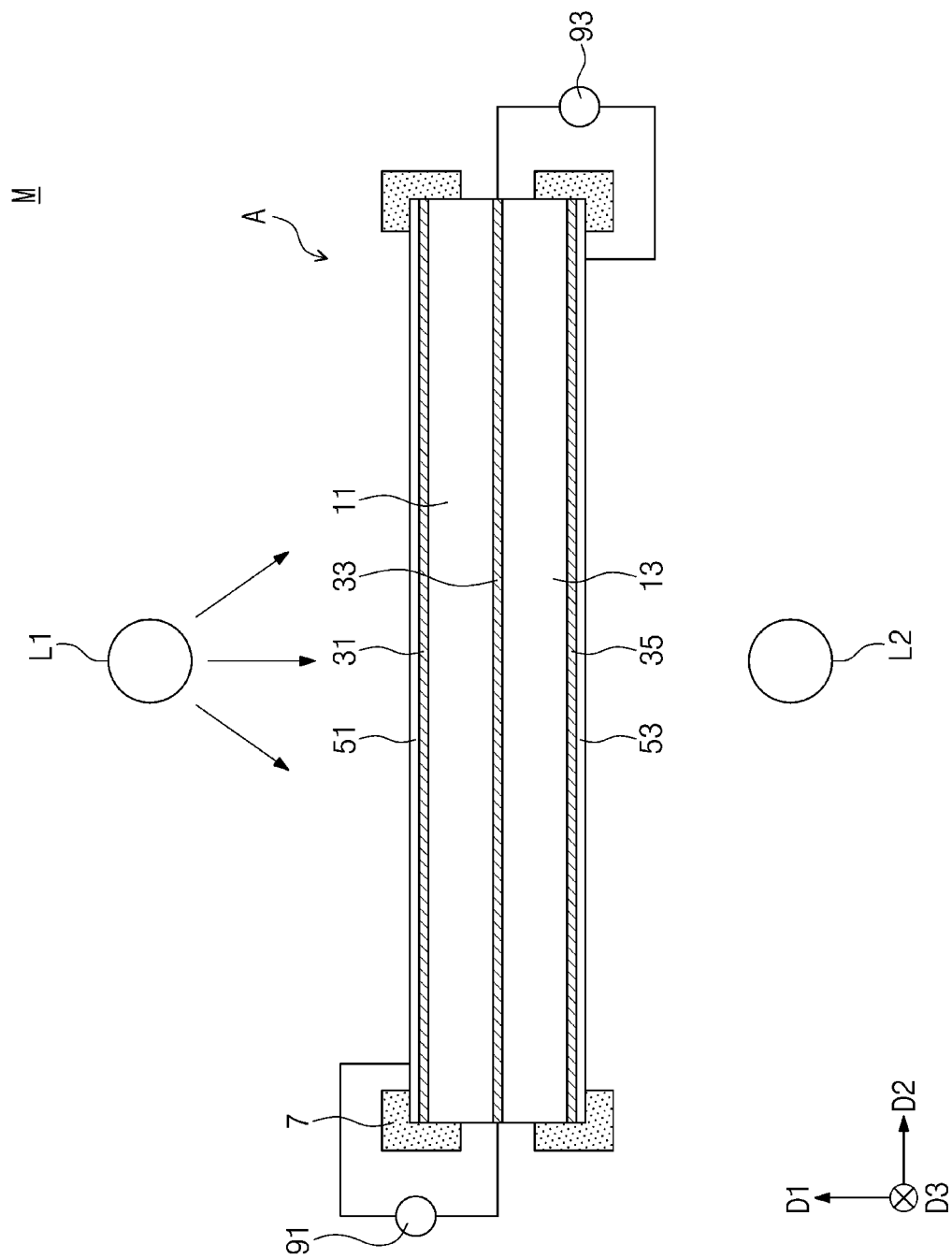
FIGS. 3 and 4 are cross-sectional views sequentially showing a state of use of a soft actuator and an artificial muscle including the same according to an exemplary embodiment of the inventive concept.
Figure 4:
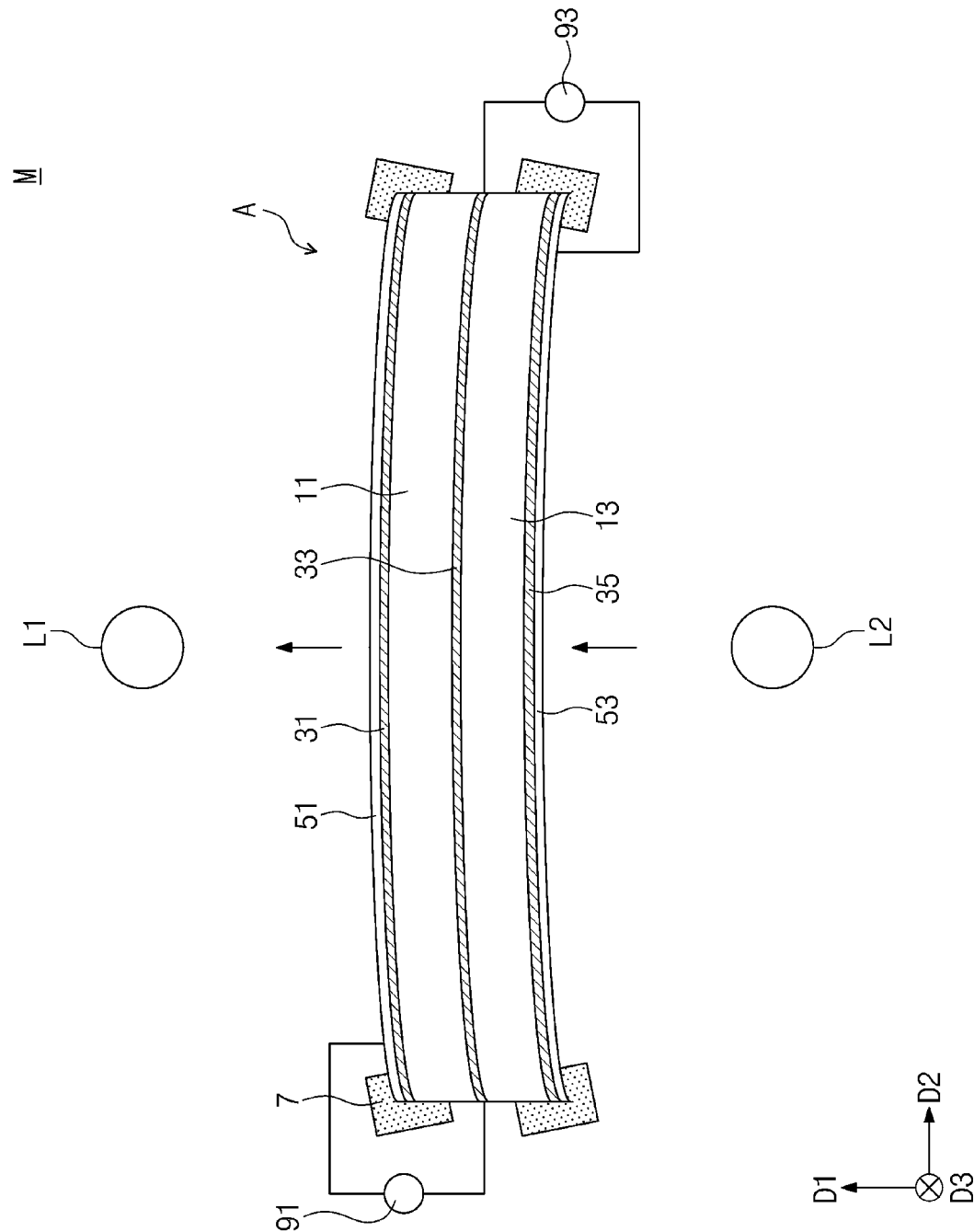

FIGS. 3 and 4 are cross-sectional views sequentially showing a state of use of a soft actuator and an artificial muscle including the same according to an exemplary embodiment of the inventive concept. Hereinafter, in FIGS. 3 and 4, the control unit of FIG. 1 may not be shown for convenience.

Referring to FIGS. 3 and 2, the irradiating of the light to the light absorption heating layer S1 may include irradiating light to the first light absorption heating layer 51 by the first light source L1 under control of the control unit C (see FIG. 1). In a state of being spaced apart from the first light absorption heating layer 51 in the first direction D1, the first light source L1 may irradiate light to the entire first light absorption heating layer 51. The first light absorption heating layer 51 may absorb at least a part of light irradiated from the first light source L1. For example, the first light absorption heating layer 51 may absorb light in a near-infrared wavelength region. The temperature of the first light absorption heating layer 51 that absorbs light may increase. The first light absorption heating layer 51 having an increased temperature may emit heat to the outside. Accordingly, heat transfer may occur from the first light absorption heating layer 51 to the second bistable polymer layer 11.

The lowering of the rigidity of the bistable polymer layer S2 may include transferring heat from the first light absorption heating layer 51 to the second bistable polymer layer 11. When heat transfer to the second bistable polymer layer 11 occurs, the temperature of the second bistable polymer layer 11 may increase. When the temperature of the second bistable polymer layer 11 rises above a certain level, at least some of the physical properties of the second bistable polymer layer 11 may be changed. For example, when the temperature of the second bistable polymer layer 11 rises above a certain level, the rigidity of the second bistable polymer layer 11 may change. More specifically, rigidity of the second bistable polymer layer 11 may be lowered.

The applying of the voltage to the flexible electrode layer S3 may include applying, by the first voltage supply unit 91, a voltage to the first flexible electrode layer 31 and the second flexible electrode layer 33 under control of the control unit C (see FIG. 1). When voltage is applied to the first flexible electrode layer 31 and the second flexible electrode layer 33, electrostatic force may be generated. More specifically, electrostatic force may be generated between the first flexible electrode layer 31 and the second flexible electrode layer 33.

Referring to FIGS. 4 and 2, the deforming of the soft actuator S4 may include deforming the second bistable polymer layer 11 by electrostatic force. The rigidity of the second bistable polymer layer 11 in which the temperature is increased may be weakened. More specifically, the rigidity of the second bistable polymer layer 11 may be lower than the rigidity of the first bistable polymer layer 13. Therefore, when a force is applied to the second bistable polymer layer 11, the second bistable polymer layer 11 may cause physical deformation. Since the rigidity of the first bistable polymer layer 13 bonded under the second bistable polymer layer 11 is relatively high, the soft actuator A may be deformed into a convex upward shape as a whole. The support structure part 7 may support or guide the deformation of the soft actuator A.

In the above, it has been described that the soft actuator A is convexly deformed using the first light source L1, but the inventive concept is not limited thereto. That is, when light is irradiated to the second light absorption heating layer 53 using the second light source L2, the above-described process occurs in the opposite direction, so that the soft actuator A may be deformed to be convex downward.

Referring to FIGS. 2 and 4, the maintaining of the soft actuator in the deformed shape S5 may include restoring the rigidity of the bistable polymer layer to its original state after the light irradiation by the light source is finished. More specifically, when the light irradiation by the first light source L1 is terminated, the temperature of the first light absorption heating layer 51 may decrease. When the temperature of the first light absorption heating layer 51 decreases, the temperature of the second bistable polymer layer 11 may also decrease. Accordingly, the rigidity of the second bistable polymer layer 11 may be restored to its original state. In embodiments, the rigidity of the second bistable polymer layer 11 may be as strong as the original. When the rigidity of the second bistable polymer layer 11 is restored to its original state, the shape of the soft actuator A may be maintained in a curved state. For example, the shape of the soft actuator A may be fixed and maintained in a convex upward state.

Referring to FIG. 2, the restoring of the shape of the soft actuator by irradiating light again S6 may include irradiating light again to the light absorption heating layer using a light source. More specifically, light may be irradiated again toward the first light absorption heating layer 51 using the first light source L1. Accordingly, the temperature of the first light absorption heating layer 51 may increase. As the temperature of the first light absorption heating layer 51 increases, the temperature of the second bistable polymer layer 11 may also increase. When the temperature of the second bistable polymer layer 11 increases, the rigidity of the second bistable polymer layer 11 may decrease again. In this process, voltage application to the first flexible electrode layer 31 and the second flexible electrode layer 33 by the first voltage supply unit 91 may not proceed. Therefore, electrostatic force may not be generated. The shape of the second bistable polymer layer 11 with lower rigidity may be restored to its original state. That is, the shape of the second bistable polymer layer 11 is restored to be flat again, so that the shape of the soft actuator A may be restored to its original state.

According to the soft actuator and the artificial muscle including the same according to exemplary embodiments of the inventive concept, the shape of the soft actuator may be maintained in a deformed state. That is, since the rigidity of the bistable polymer layer changes according to temperature, it may be easy to allow the bistable polymer layer to maintain its shape in a curved state by using this.

According to the soft actuator and the artificial muscle including the same according to exemplary embodiments of the inventive concept, the bistable polymer layer may be deformed by using a characteristic in which rigidity varies depending on temperature. Therefore, it may not be necessary to use complex structures to change the rigidity. Accordingly, the overall structure of the soft actuator may be simplified and the volume may be reduced. In addition, since it is driven by a slim soft actuator, precise control may be possible.

Figure 5:
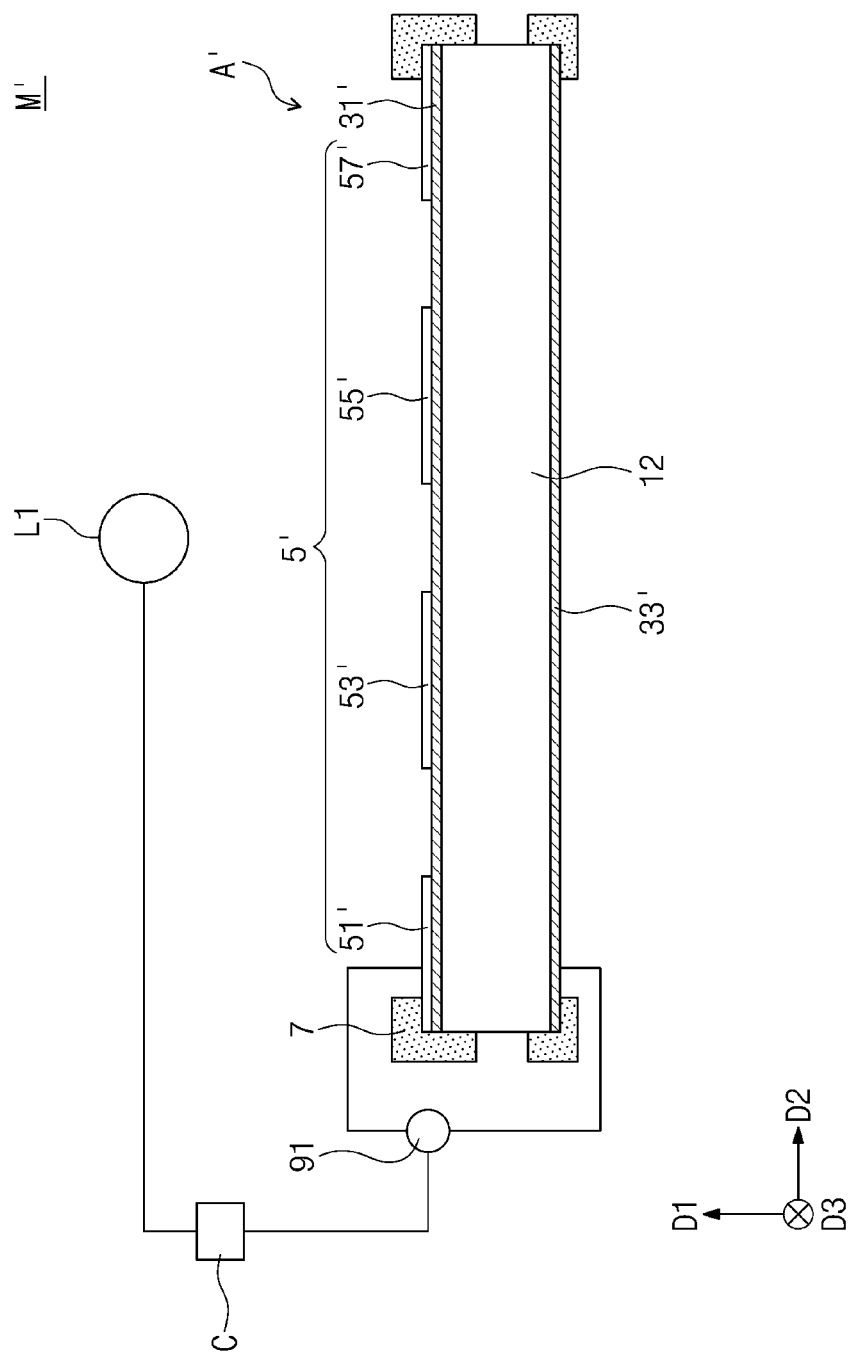
FIG. 5 is a cross-sectional view showing a soft actuator and an artificial muscle including the same according to an exemplary embodiment of the inventive concept.

FIG. 5 is a cross-sectional view showing a soft actuator and an artificial muscle including the same according to an exemplary embodiment of the inventive concept.

Hereinafter, descriptions of contents that are substantially the same or similar to those described with reference to FIGS. 1 to 4 may be omitted for convenience.

Referring to FIG. 5, the artificial muscle M' may include a bistable polymer layer 12, a first flexible electrode layer 31', a second flexible electrode layer 33', a light absorption heating layer 5', a support structure part 7, and a voltage supply unit 91.

The bistable polymer layer 12 may be similar to the bistable polymer layer described with reference to FIG. 1 and the like. The bistable polymer layer 12 may include a material that is substantially the same as or similar to the bistable polymer layer described with reference to FIG. 1 and the like. The first flexible electrode layer 31' may be located on the upper surface of the bistable polymer layer 12. The second flexible electrode layer 33' may be located on the lower surface of the bistable polymer layer 12.

The light absorption heating layer 5' may be located on the upper surface of the first flexible electrode layer 31'. The light absorption heating layer 5' may include a material that is substantially the same as or similar to the light absorption heating layer described with reference to FIG. 1 and the like. The light absorption heating layer 5' may be patterned. That is, the light absorption heating layer 5' may be patterned to provide patterning holes. The light absorption heating layer 5' may provide a plurality of light absorption heating layers 51', 53', 55', and 57' that are horizontally spaced apart from each other with a patterning hole therebetween. Through the patterning hole, a part of the first flexible electrode layer 31' may be exposed. In other words, a part of the first flexible electrode layer 31' may be exposed by the patterned light absorption heating layer 5'.

The voltage supply unit 91 may be electrically connected to the first flexible electrode layer 31' and the second flexible electrode layer 33'.

According to the soft actuator and the artificial muscle including the same according to exemplary embodiments of the inventive concept, since the light absorption heating layer is patterned, when light irradiation by a light source is performed, the temperature of only some areas may rise. In other words, only the temperature of the bistable polymer layer under the light absorption heating layer may be raised. Accordingly, only some areas of the bistable polymer layer may change rigidity. That is, only a part of the bistable polymer layer may be bent. Thus, the soft actuator may be bent with multiple curvatures. Accordingly, it may be possible to more accurately simulate the muscle movement of the human body.

According to the soft actuator and the artificial muscle including the same according to exemplary embodiments of the inventive concept, a simple manufacturing process called patterning of the light absorption heating layer makes it possible to provide a soft actuator that bends with multiple curvatures. That is, it may be possible to manufacture variously bent artificial muscles with a simple process.

Figure 6:
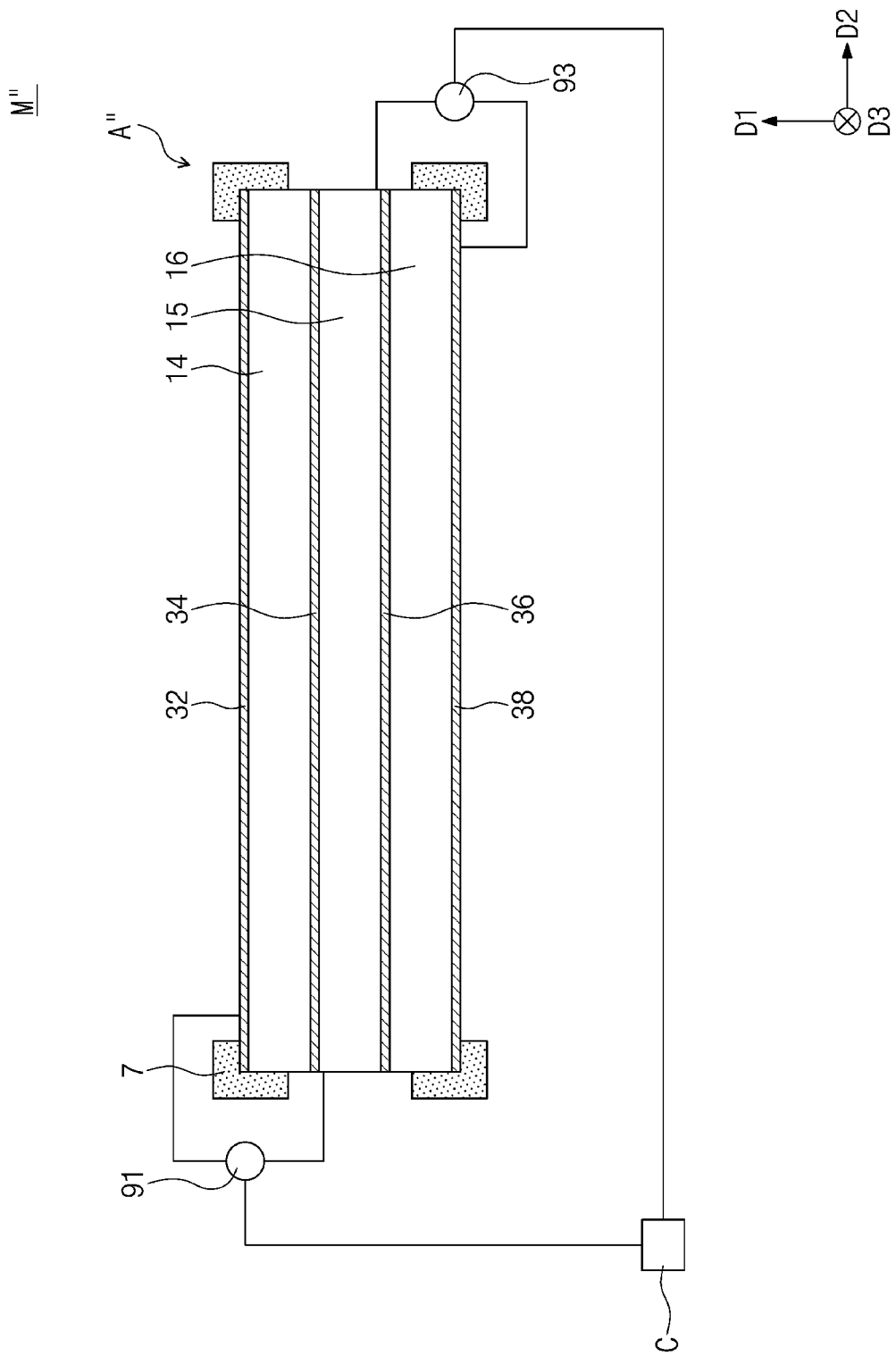
FIG. 6 is a cross-sectional view showing a soft actuator and an artificial muscle including the same according to an exemplary embodiment of the inventive concept.

FIG. 6 is a cross-sectional view showing a soft actuator and an artificial muscle including the same according to an exemplary embodiment of the inventive concept.

Hereinafter, descriptions of contents that are substantially the same or similar to those described with reference to FIGS. 1 to 5 may be omitted for convenience.

Referring to FIG. 6, the artificial muscle M" may include a support layer 15, a first strain layer 14, a second strain layer 16, a first flexible electrode layer 32, a second flexible electrode layer 34, a third flexible electrode layer 36, and a fourth flexible electrode layer 38. The support layer 15 may include a material having higher rigidity than the first strain layer 14 and the second strain layer 16. The first strain layer 14 and the second strain layer 16 may face each other with the support layer 15 interposed therebetween. The first strain layer 14 and the second strain layer 16 may include a dielectric elastic polymer. The dielectric elastic polymer may be prepared by mixing a prepolymer and a crosslinker. If the composition ratio of the two materials (Crosslinker/Prepolymer, C/P) is different, the rigidity of the dielectric elastic polymer may be controlled. The first flexible electrode layer 32, the second flexible electrode layer 34, the third flexible electrode layer 36, and the fourth flexible electrode layer 38 may be coupled between the support layer 15, the first strain layer 14, and the second strain layer 16, and to the upper and lower surfaces thereof. When voltage is applied to the first flexible electrode layer 32, the second flexible electrode layer 34, the third flexible electrode layer 36, and the fourth flexible electrode layer 38, the soft actuator A" may be convex upward or convex downward due to electrostatic force.

Figure 7:
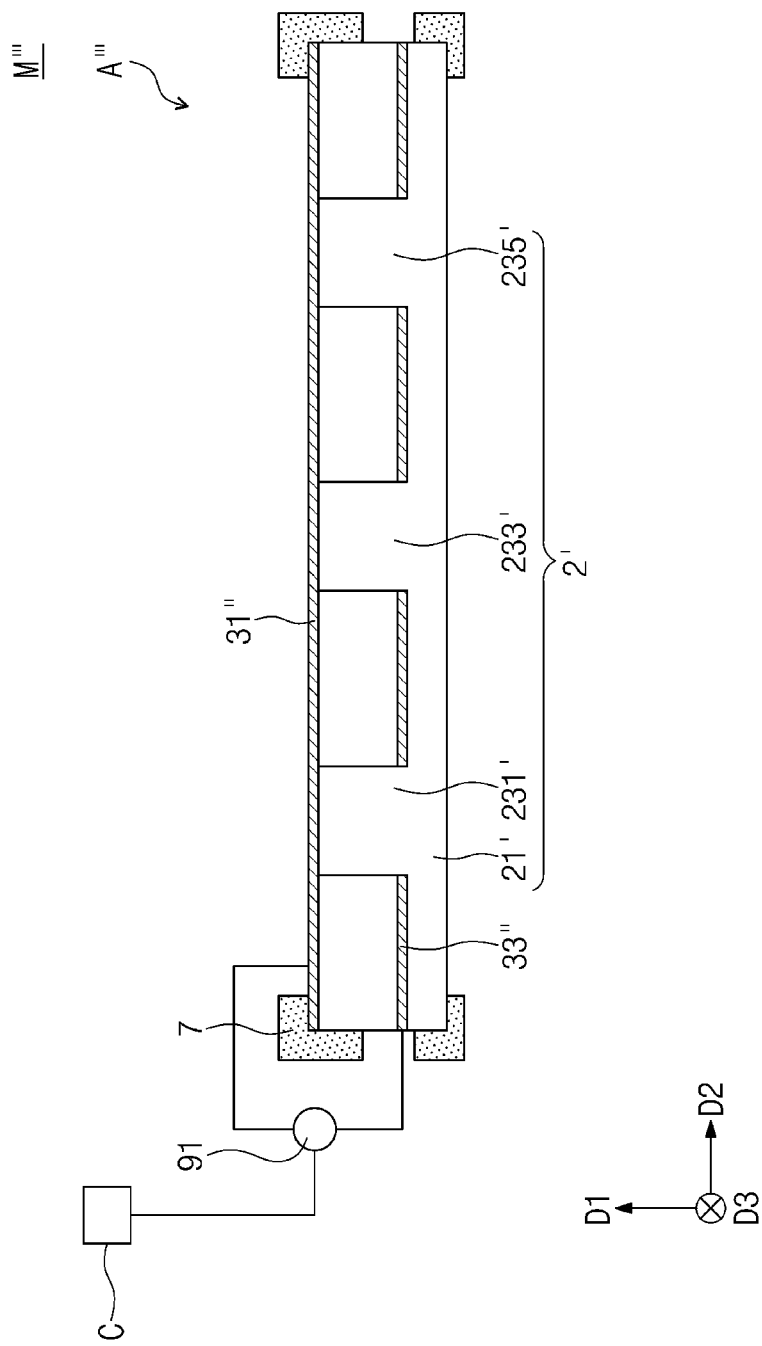
FIG. 7 is a cross-sectional view showing a soft actuator and an artificial muscle including the same according to an exemplary embodiment of the inventive concept.

FIG. 7 is a cross-sectional view showing a soft actuator and an artificial muscle including the same according to an exemplary embodiment of the inventive concept.

Hereinafter, descriptions of contents that are substantially the same or similar to those described with reference to FIGS. 1 to 6 may be omitted for convenience.

Referring to FIG. 7, unlike that described with reference to FIG. 6, the support layer 2' may include a lower support 21' and a plurality of division supports 231', 233', and 235'. When a voltage is applied to the first flexible electrode layer 31" and the second flexible electrode layer 33' by the voltage supply unit 91, the soft actuator A'" may be bent with various curvatures.

Figure 8:
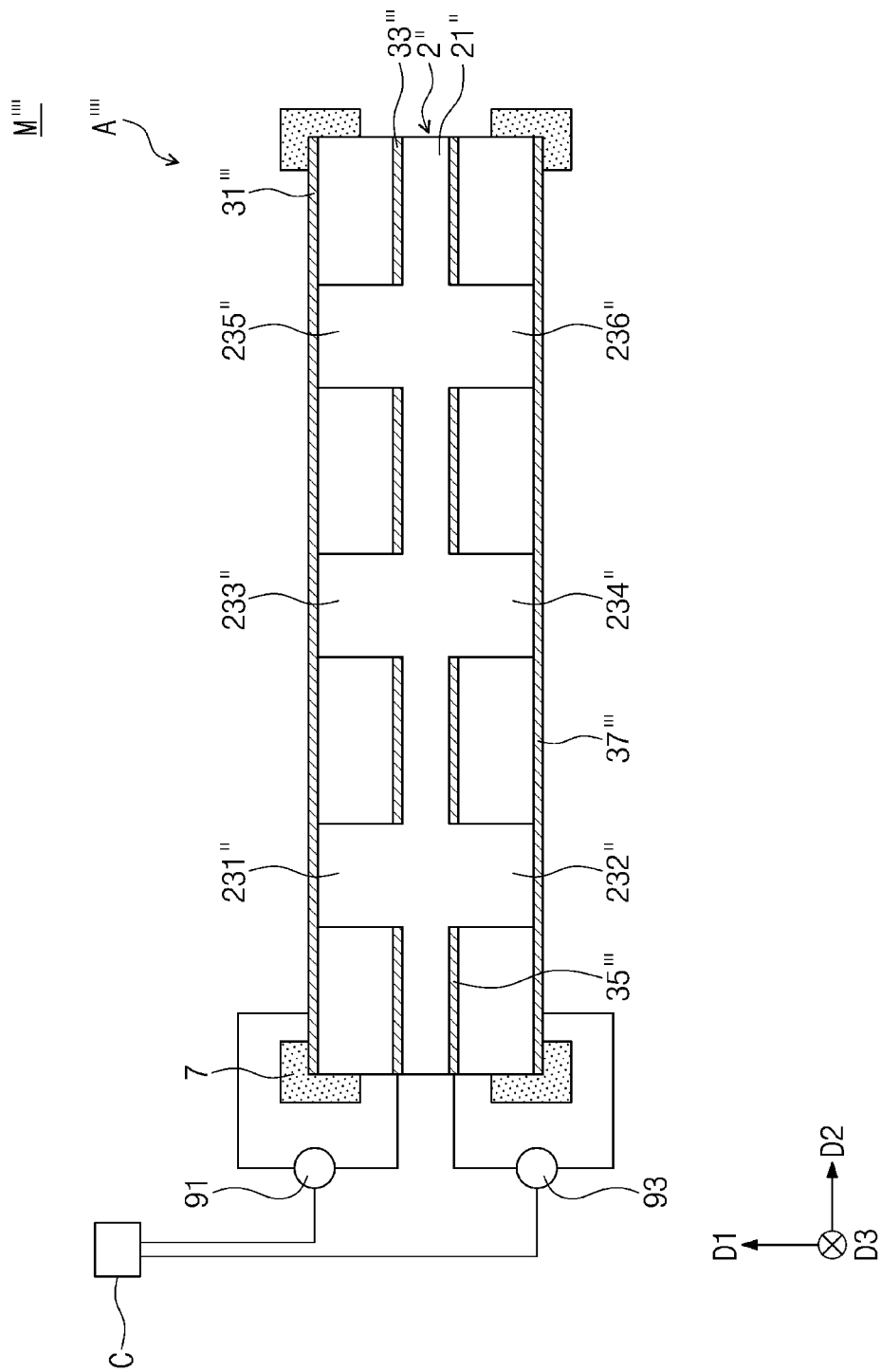
FIG. 8 is a cross-sectional view showing a soft actuator and an artificial muscle including the same according to an exemplary embodiment of the inventive concept.

FIG. 8 is a cross-sectional view showing a soft actuator and an artificial muscle including the same according to an exemplary embodiment of the inventive concept.

Hereinafter, descriptions of contents that are substantially the same or similar to those described with reference to FIGS. 1 to 7 may be omitted for convenience.

Referring to FIG. 8, unlike that described with reference to FIG. 7, in relation to the artificial muscles M"", a support layer 2" may include a central support 21", upper division supports 231", 233", and 235" and lower division supports 232", 235", and 236". When a voltage is applied to the first flexible electrode layer 31'" and the second flexible electrode layer 33'" by the first voltage supply unit 91, the soft actuators A"" may be convex upward. When voltage is applied to the third flexible electrode layer 35'" and the fourth flexible electrode layer 37'" by the second voltage supply unit 93, the soft actuator A"" may be convex downward.

According to the soft actuator and the artificial muscle including the same according to an exemplary embodiment of the inventive concept, precise control may be possible.

According to the soft actuator and the artificial muscle including the same according to an exemplary embodiment of the inventive concept, the volume may be small and slim.

According to the soft actuator and the artificial muscle including the same according to an exemplary embodiment of the inventive concept, it is possible to bend with a plurality of curvatures.

The effects of the inventive concept are not limited to the problems mentioned above, and other effects not mentioned will be clearly understood by those skilled in the art from the following description.

Although the exemplary embodiments of the inventive concept have been described, it is understood that the inventive concept should not be limited to these exemplary embodiments but various changes and modifications may be made by one ordinary skilled in the art within the spirit and scope of the inventive concept as hereinafter claimed.

What is claimed is:
1. A soft actuator comprising:
a first bistable polymer layer;
a second bistable polymer layer on the first bistable polymer layer;
a first flexible electrode layer on an upper surface of the second bistable polymer layer;

a second flexible electrode layer between the first bistable polymer layer and the second bistable polymer layer;
a first light absorption heating layer disposed on the first flexible electrode layer and configured to increase a temperature when light is absorbed;
a third flexible electrode layer on a lower surface of the first bistable polymer layer; and
a first voltage supply unit,
wherein the first voltage supply unit is electrically connected to the first flexible electrode layer and the second flexible electrode layer.

2. The soft actuator of claim 1, wherein the first light absorption heating layer comprises a PEDOT-based material.

3. The soft actuator of claim 1, further comprising a second light absorption heating layer coupled under the third flexible electrode layer.

4. The soft actuator of claim 1, further comprising a second voltage supply unit,
wherein the second voltage supply unit is electrically connected to the second flexible electrode layer and the third flexible electrode layer.

5. The soft actuator of claim 1, further comprising a support structure part coupled to an upper surface of the first light absorption heating layer and a side surface of the second bistable polymer layer.

6. An artificial muscle comprising:
a soft actuator;
a light source; and
a control unit,
wherein the soft actuator comprises:
a first bistable polymer layer;
a second bistable polymer layer on the first bistable polymer layer;
a first flexible electrode layer on an upper surface of the second bistable polymer layer;
a second flexible electrode layer between the first bistable polymer layer and the second bistable polymer layer;
a first light absorption heating layer disposed on the first flexible electrode layer and configured to increase a temperature when light is absorbed;
a first voltage supply unit; and
a support structure part coupled to an upper surface of the first light absorption heating layer and a side surface of the second bistable polymer layer,
wherein the first voltage supply unit is electrically connected to the first flexible electrode layer and the second flexible electrode layer,
wherein the control unit controls the light source and the first voltage supply unit.

7. The artificial muscle of claim 6, further comprising:
a third flexible electrode layer on a lower surface of the first bistable polymer layer; and
a second light absorption heating layer coupled under the third flexible electrode layer.

8. The artificial muscle of claim 7, further comprising a second voltage supply unit,
wherein the second voltage supply unit is electrically connected to the second flexible electrode layer and the third flexible electrode layer.

9. The artificial muscle of claim 7, wherein each of the first light absorption heating layer and the second light absorption heating layer comprises a PEDOT-based material.

10. The artificial muscle of claim 7, wherein the light source comprises a first light source that irradiates light to the first light absorption heating layer and a second light source that irradiates light to the second light absorption heating layer.

11. An artificial muscle comprising:
a soft actuator; and
a light source configured to irradiate light to the soft actuator,
wherein the soft actuator comprises:
a bistable polymer layer;
a first flexible electrode layer on an upper surface of the bistable polymer layer;
a second flexible electrode layer on a lower surface of the bistable polymer layer;
a light absorption heating layer disposed on the first flexible electrode layer and configured to increase a temperature when light is absorbed; and
a voltage supply unit,
wherein the voltage supply unit is electrically connected to the first flexible electrode layer and the second flexible electrode layer,
wherein the light absorption heating layer is patterned, so that a part of the first flexible electrode layer is exposed between the patterned light absorption heating layer.

12. The artificial muscle of claim 11, wherein the light absorption heating layer comprises a PEDOT-based material.

13. The artificial muscle of claim 11, further comprising a support structure part coupled to an upper surface of the light absorption heating layer or a side surface of the second bistable polymer layer.

* * * * *